United States Patent
Majeed et al.

(10) Patent No.: US 10,653,643 B2
(45) Date of Patent: May 19, 2020

(54) LIVER PROTECTANT COMPOSITIONS AND THERAPEUTIC APPLICATIONS

(71) Applicants: Muhammed Majeed, Edison, NJ (US); Kalyanam Nagabhushanam, East Windsor, NJ (US); Lakshmi Mundkur, Bangalore (IN)

(72) Inventors: Muhammed Majeed, Edison, NJ (US); Kalyanam Nagabhushanam, East Windsor, NJ (US); Lakshmi Mundkur, Bangalore (IN)

(73) Assignee: SAMI LABS LIMITED, Bangalore (IN)

( * ) Notice: Subject to any disclaimer, the term of this patent is extended or adjusted under 35 U.S.C. 154(b) by 0 days.

(21) Appl. No.: 16/360,283

(22) Filed: Mar. 21, 2019

(65) Prior Publication Data
US 2019/0290599 A1    Sep. 26, 2019

Related U.S. Application Data

(60) Provisional application No. 62/647,041, filed on Mar. 23, 2018.

(51) Int. Cl.
*A61K 31/122* (2006.01)
*A61K 31/12* (2006.01)
*A23L 33/105* (2016.01)
*A61P 1/16* (2006.01)

(52) U.S. Cl.
CPC ............ *A61K 31/12* (2013.01); *A23L 33/105* (2016.08); *A61K 31/122* (2013.01); *A61P 1/16* (2018.01); *A23V 2002/00* (2013.01)

(58) Field of Classification Search
CPC .................................................. A61K 31/122
See application file for complete search history.

(56) References Cited

U.S. PATENT DOCUMENTS

2013/0281544 A1* 10/2013 Majeed ................ A61K 31/122
514/681

OTHER PUBLICATIONS

Rahmani et al., Phytotherapy Research, 2016, 30(9): 1540-1548.*
Haubert et al. Nutr Metab Insights, 2015, 4:1-6.(abstract).*
Sarah Deweerdt (2017) "Divergent paths: Outlook—Fatty liver disease" Nature 551, S92-S93,doi: 10.1038/d41586-017-06925-2.
Wong et al., (2010) "Disease progression of non-alcoholic fatty liver disease: a prospective study with paired liver biopsies at 3 years" Gut, 59:969-974.
Ratziu et al., (2016), Elafibranor, an Agonist of the Peroxisome Proliferator-Activated Receptor-α and -δ, Induces Resolution of Nonalcoholic Steatohepatitis Without Fibrosis Worsening Gastroenterology, 150: 1147-59.
Loomba et al., (2018) "The ASK1 inhibitor selonsertib in patients with nonalcoholic steatohepatitis: A randomized, phase 2 trial" Hepatology, 67: 549-59.
Hinz, et al., (2012). "Recent developments in myofibroblast biology: paradigms for connective tissue remodeling." Am J Pathol 180(4): 1340-1355.
Zhang, et. al., (1994). "Myofibroblasts and their role in lung collagen gene expression during pulmonary fibrosis. A combined immunohistochemical and in situ hybridization study." Am J Pathol 145(1): 114-125.
Brenner, et al., (2012). "Origin of myofibroblasts in liver fibrosis." Fibrogenesis Tissue Repair 5(Suppl 1): S17.
Rull, et al., (2009). "Hepatic monocyte chemoattractant protein-1 is upregulated by dietary cholesterol and contributes to liver steatosis." Cytokine 48(3): 273-279.

* cited by examiner

*Primary Examiner* — Rei Tsang Shiao

(57) ABSTRACT

The invention pertains to a composition comprising Curcuminoids and Garcinol for hepatoprotection. Specifically, the invention discloses a composition comprising 95% Curcuminoids and 20% Garcinol for the therapeutic management of Non-alcoholic fatty liver disease (NAFLD) and associated conditions like steatosis, Non-alcoholic steatoheapatitis (NASH), fibrosis and cirrhosis of the liver.

11 Claims, 7 Drawing Sheets
(2 of 7 Drawing Sheet(s) Filed in Color)

Specification includes a Sequence Listing.

SEQUENCE LISTING

<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<223> OTHER INFORMATION: Forward primer for beta-actin

<400> SEQUENCE: 1
gaagtccctc accctcccaa                                               20

<210> SEQ ID NO 2
<211> LENGTH: 16
<212> TYPE: DNA
<213> ORGANISM: Artificial Sequence
<220> FEATURE:
<223> OTHER INFORMATION: Reverse Primer for beta-actin

<400> SEQUENCE: 2
ggcatggacg cgacca                                                   16

<210> SEQ ID NO 3
<211> LENGTH: 24
<212> TYPE: DNA
<213> ORGANISM: Artificial sequence
<220> FEATURE:
<223> OTHER INFORMATION: Forward primer for NFkappaB

<400> SEQUENCE: 3
gaaattcctg atccagacaa aaac                                          24

<210> SEQ ID NO 4
<211> LENGTH: 24
<212> TYPE: DNA
<213> ORGANISM: Artificial sequence

```
<220> FEATURE:
<223> OTHER INFORMATION: Reverse primer for NFkappaB

<400> SEQUENCE: 4
atcacttcaa tggcctctgt gtag                                              24

<210> SEQ ID NO 5
<211> LENGTH: 19
<212> TYPE: DNA
<213> ORGANISM: Artificial sequence
<220> FEATURE:
<223> OTHER INFORMATION: Forward primer for TNF-alpha

<400> SEQUENCE: 5
ctccaggcgg tgcctatgt                                                    19

<210> SEQ ID NO 6
<211> LENGTH: 17
<212> TYPE: DNA
<213> ORGANISM: Artificial sequence
<220> FEATURE:
<223> OTHER INFORMATION: Reverse primer for TNF-alpha

<400> SEQUENCE: 6
gaagagcgtg gtggccc                                                      17

<210> SEQ ID NO 7
<211> LENGTH: 19
<212> TYPE: DNA
<213> ORGANISM: Artificial sequence
<220> FEATURE:
<223> OTHER INFORMATION: Forward primer for MCP-1

<400> SEQUENCE: 7
gcatccacgt gttggctca                                                    19

<210> SEQ ID NO 8
<211> LENGTH: 23
<212> TYPE: DNA
<213> ORGANISM: Artificial sequence
<220> FEATURE:
<223> OTHER INFORMATION: Reverse primer for MCP-1

<400> SEQUENCE: 8
ctccagccta ctcattggga tca                                               23

<210> SEQ ID NO 9
<211> LENGTH: 22
<212> TYPE: DNA
<213> ORGANISM: Artificial sequence
<220> FEATURE:
<223> OTHER INFORMATION: Forward primer for TGF-beta

<400> SEQUENCE: 9
ttgccctcta caaccaacac aa                                                22

<210> SEQ ID NO 10
<211> LENGTH: 20
<212> TYPE: DNA
<213> ORGANISM: Artificial sequence
<220> FEATURE:
<223> OTHER INFORMATION: Reverse primer for TGF-beta

<400> SEQUENCE: 10
ggcttgcgac ccacgtagta                                                   20
```

```
<210> SEQ ID NO 11
<211> LENGTH: 21
<212> TYPE: DNA
<213> ORGANISM: Artificial sequence
<220> FEATURE:
<223> OTHER INFORMATION: Forward primer for Collagen1

<400> SEQUENCE: 11
ttccctggac ctaagggtac t                                             21

<210> SEQ ID NO 12
<211> LENGTH: 18
<212> TYPE: DNA
<213> ORGANISM: Artificial sequence
<220> FEATURE:
<223> OTHER INFORMATION: Reverse primer for Collagen1

<400> SEQUENCE: 12
ttgagctcca gcttcgcc                                                 18
```

LIVER PROTECTANT COMPOSITIONS AND THERAPEUTIC APPLICATIONS

CROSS-REFERENCE TO RELATED APPLICATIONS

This is a non-provisional application claiming priority from U.S. provisional application No. 62/647,041 filed on 23 Mar. 2018.

FIELD OF INVENTION

The present invention relates to liver protectant compositions. Specifically, the invention relates to a composition comprising Curcuminoids and Garcinol for hepatoprotection. More specifically, the invention relates to a composition comprising 95% Curcuminoids and 20% Garcinol for the therapeutic management of Non-alcoholic fatty liver disease (NAFLD) and associated conditions.

BACKGROUND OF THE INVENTION

Non-alcoholic fatty liver diseases (NAFLDs) include a spectrum of fatty liver diseases in the absence of alcohol consumption, ranging from fatty liver to cirrhosis and hepatocellular carcinoma. Different degrees or types of NAFLDs include a) Steatosis b) Non-alcoholic steatoheapatitis (NASH) c) Fibrosis and d) cirrhosis e) Hepatocellular carcinoma. Steatosis is defined as triglyceride accumulation in hepatocytes or excess fat in liver. A minimum excess overload of fat of at least 5-10% than normal is considered significant condition of steatosis.

The second stage of NAFLD, Non alcohol steatoheapatitis (NASH), is a potentially serious condition that carries a substantial risk of progression to end stage Fibrosis, cirrhosis, and liver cancer or Hepatocellular carcinoma. The histopathological features of nonalcoholic steatoheapatitis (NASH) include hepatocellular steatosis and ballooning, mixed acute and chronic inflammation and perivenular, perisinusoidal collagen deposition. NASH is considered as the hepatic manifestation of metabolic disorder and is closely associated with type 2 diabetes, obesity, insulin resistance and systemic inflammatory state. The following prior art documents disclose the characteristic features of NAFLD and NASH a) Williams, C. D., et al., Prevalence of nonalcoholic fatty liver disease and nonalcoholic steatohepatitis among a largely middle-aged population utilizing ultrasound and liver biopsy: a prospective study. Gastroenterology, 2011; 140(1): 124-31.
b) Charlton, M. R., et al., Frequency and outcomes of liver transplantation for nonalcoholic steatohepatitis in the United States. Gastroenterology, 2011; 141(4):1249-53.
c) Sanyal, A., et al., Population-based risk factors and resource utilization for HCC: US perspective. Curr Med Res Opin, 2010; 26(9):2183-91.
d) Ratziu, V., et al., A position statement on NAFLD/NASH based on the EASL 2009 special conference. J Hepatol, 2010; 53(2): 372-84.
e) Yki-Jarvinen, H., Non-alcoholic fatty liver disease as a cause and a consequence of metabolic syndrome. Lancet Diabetes Endocrinol, 2014; 2(11): 901-10.

Evaluating the histopathology of NASH and NAFLD is important for determining the degree and progression of the disease. A histological 'grading and staging" system has been developed to reflect the unique features of steatoheapatitis, gradations of severity and fibrosis, and to promote uniform reporting of the histopathology; (Brunt et al., Non-alcoholic steatoheapatitis: definition and pathology; Semin Liver Dis. 2001; 21(1):3-16), wherein a staging score reflects both location and extent of the disease.

Other NAFLDs may be differentiated from NASH by the NAFLD activity score (NAS), the sum of histopathology scores of a liver biopsy for Steatosis (0-3 grades), lobular inflammation (0-2), and hepatocellular ballooning (0-2). A NAS of less than 3 corresponds to NAFLD, 3-4 corresponds to borderline NASH, and greater than 5 corresponds to NASH. The biopsy is also scored for fibrosis (0-4). Similarly the grading system for ballooning and lobular inflammation, portal inflammation and steatosis grade is well explained and differentiated by Kleiner et al., Histology of NAFLD and NASH in adults and children, Clin Liver Dis. 2016; 20(2): 293-312.

Fibrosis occurs on further metabolic and biochemical abnormalities. It depends on the imbalance between the rate of formation and deposition of collagen. Fibrosis stages include stage 1, zone 3 perisinusoidal fibrosis; stage 2, perisinusoidal fibrosis with portal fibrosis; stage 3, as above with bridging fibrosis; and stage 4 as described by Brunt et al., Non alcoholic steatohepatits: a proposal for grading and staging the histological lesions. Am J Gastroenterol. 1999; 94(9):2467-74. Fibrosis can be diagnosed in liver diseases using hydroxyproline and oxidative stress as biomarkers (Gabr et al., Prediction of fibrosis in hepatitis C. patients: assessments using hydroxyproline and oxidative stress biomarkers. Indian Virological Society 2013; 25(1): 91-100)

The oxidative stress markers also play a significant role in maintaining liver health. The importance of oxidative stress marker as non-invasive parameter for the assessment of liver fibrosis (Novitskiy G et al., Effects of ethanol and acetaldehyde on reactive oxygen species production in rat hepatic stellate cells Alcohol Clin Exp Res. 2006; 30(8):1429-35). Oxidative stress markers, antioxidant enzymes and hydroxyproline are documented to play a part in the pathogenesis of CHC. Clichici S et al., Non-invasive oxidative stress markers for liver fibrosis development in the evolution of toxic hepatitis. Acta Physiol Hung. 2011; 98(2):195-204)

NASH is usually a silent disease with minimum symptoms, while weight loss, fatigue and weakness develop as the disease progresses. Individuals with fatty liver of NAFLDs are determined to have elevated liver enzymes and lowering the liver enzyme population will correct or improve the liver condition. State-of-the art technique to manage enzyme count is to provide glutamine, a natural amino acid used as a nutritional supplement.

There is an urgent need for therapeutic management of NAFLDs. It is a significant burden to public health system, with no approved drugs for treatment. The primary mode of treatment is lifestyle management, while pioglitazone and Vitamin E have been used as pharmacotherapy to reduce hepatocellular injury, fibrosis and improve steatohepatitis. Other methods include using insulin sensitizers, biguanides eg. Metformin.

Natural molecules from different plant sources are also currently being used for hepatoprotection and for the management of NAFLDs (Madrigal-Santillán et al., Review of natural products with hepatoprotective effects, World J Gastroenterol. 2014; 20(40): 14787-14804). Curcumin from *Curcuma* sp. is well known for its therapeutic effect in mitigating the symptoms of NASH (Rahmani et al., Treatment of Non-alcoholic Fatty Liver Disease with Curcumin: A Randomized Placebo-controlled Trial, Phytotherapy Research, 2016; 30(9):1540-1548; Amato et al., NAFLD and Atherosclerosis Are Prevented by a Natural Dietary Supplement Containing Curcumin, Silymarin, Guggul, Chlorogenic Acid and Inulin in Mice Fed a High-Fat Diet, Nutrients 2017, 9(5), 492; https://doi.org/10.3390/nu9050492). Garcinol from *Garcinia* sp. is also a known hepatoprotective agent (WO2012092430A1). However, most of the natural molecules do not confer complete protection against all symptoms of NAFLDs. There still exists an unmet industrial need for a composition which is safe and reliable and elicits hepatoprotective ability by mitigating most of the symptoms associated with NAFLD and NASH.

The present invention provides a synergistic composition comprising curcuminoids and garcinol for the therapeutic management of NAFLDs and associated conditions like NASH, fibrosis and cirrhosis.

It is the principle object of the invention to disclose a synergistic hepatoprotective composition comprising 95% w/w Curcuminoids and 20% w/w Garcinol for the management of NAFDLs and associated conditions thereof.

It is yet another object of the invention to disclose a method for the therapeutic management of NAFLD and associated conditions like steatosis, NASH, fibrosis and cirrhosis using a composition comprising 95% w/w Curcuminoids and 20% w/w Garcinol.

The present invention solves the abovementioned objectives and provides further related advantages.

SUMMARY OF THE INVENTION

The present invention relates to a composition comprising 95% w/w Curcuminoids and 20% w/w Garcinol for use as a Hepatoprotective agent. More specifically, the invention discloses the use of a composition comprising 95% w/w Curcuminoids and 20% w/w Garcinol for the therapeutic management of NAFLDs and associated conditions like steatosis, NASH, liver fibrosis and cirrhosis.

The invention also discloses a method for the therapeutic management of NAFLDs and related conditions like steatosis, NASH, fibrosis and cirrhosis by administering a composition comprising 95% w/w Curcuminoids and 20% w/w Garcinol.

Other features and advantages of the present invention will become apparent from the following more detailed description, taken in conjunction with the accompanying images, which illustrate, by way of example, the principle of the invention.

BRIEF DESCRIPTION OF DRAWINGS

The patent or application file contains at least one drawing executed in color. Copies of this patent or patent application publication with color drawing(s) will be provided by the office upon request and payment of the necessary fee.

DESCRIPTION OF MOST PREFERRED EMBODIMENTS

Figure 1:
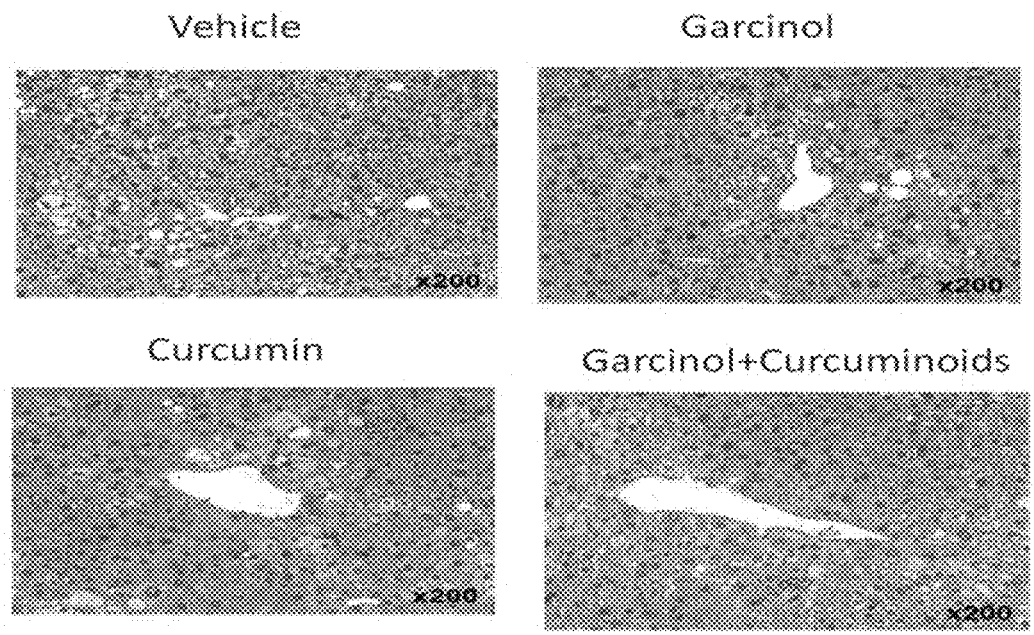
FIG. 1 shows the histopathological sections of liver stained with Haematoxylin and Eosin

In a most preferred embodiment, the invention discloses a method for the therapeutic management of NAFLD and associated conditions in mammals, said method comprising steps of administering effective amounts of a composition containing 95% Curcuminoids and 20% Garcinol to mammals in need of such therapy, to bring about a reduction in symptoms of NAFLD and related conditions. In a related embodiment, the associated conditions of NAFLD include non-alcoholic fatty liver (NAFL), non-alcoholic steatohepatitis (NASH), Fibrosis and cirrhosis. In related embodiment, the symptoms of NAFL include abnormal build-up of fat in the hepatocytes.

In related embodiment, the symptoms NASH include, but not limited to, inflammatory infiltration and hepatocellular ballooning. In another related embodiment the symptoms of fibrosis include elevated hydroxyproline levels and pathological deposition of collagen in liver. In another related embodiment, the symptoms of NAFLD and associated conditions include increased expression of inflammatory markers, elevated liver enzyme levels, increased lipid peroxidation, decreased antioxidant levels, increased collagen expression and reduced adiponectin levels.

In yet another related embodiment, the inflammatory markers are selected from the group comprising TNF-α, NFκB, TGF-β and MCP-1.

In yet another aspect, the liver enzyme is preferably ALT. In another related aspect, the antioxidants are selected from the group comprising glutathione and glutathione peroxidase. In a related embodiment, the 95% Curcuminoids and 20% Garcinol in the composition are administered in concentrations of about 10-50 mg/kg bodyweight and 1-10 mg/kg bodyweight respectively.

In another related embodiment, the 95% Curcuminoids are present in the ratio of about 75-81% curcumin, 15-19% demethoxy curcumin, and 2.2-6.5% bis demethoxy curcumin. In another related aspect, the 20% garcinol is obtained from *Garcinia* sp. In a preferred embodiment, the *Garcinia* sp. is *Garcinia indica*. In another related aspect, the mammal is human.

In yet another aspect, the composition is formulated with pharmaceutically/nutraceutically accepted excipients and adjuvants and administered orally in the form of tablets, capsules, syrups, gummies, powders, suspensions, emulsions, chewable, candies or eatables. In another related aspect, the composition comprising 95% Curcuminoids and 20% Garcinol can be formulated with other known ingredients for liver protection.

In another preferred embodiment, the invention discloses a composition comprising 95% Curcuminoids and 20% Garcinol for the therapeutic management of NAFLD and associated conditions in mammals. In a related embodiment, the associated conditions of NAFLD include NAFL, NASH, fibrosis and cirrhosis. In related embodiment, the symptoms of NAFL include abnormal build-up of fat in the hepatocytes. In related embodiment, the symptoms NASH include, but not limited to, inflammatory infiltration and hepatocellular ballooning.

In another related embodiment the symptoms of fibrosis include elevated hydroxyproline levels and pathological deposition of collagen in liver. In another related embodiment, the symptoms of NAFLD and associated conditions include increased expression of inflammatory markers, elevated liver enzyme levels, increased lipid peroxidation, decreased antioxidant levels, increased collagen expression and reduced adiponectin levels. In yet another related embodiment, the inflammatory markers are selected from the group comprising TNF-α, NFκB, TGF-β and MCP-1.

In yet another aspect, the liver enzyme is preferably ALT. In another related aspect, the antioxidants are selected from the group comprising glutathione and glutathione peroxidase. In a related embodiment, the 95% Curcuminoids and 20% Garcinol in the composition are administered in concentrations of about 10-50 mg/kg bodyweight and 1-10 mg/kg bodyweight respectively. In another related embodiment, the 95% Curcuminoids are present in the ratio of about 75-81% curcumin, 15-19% demethoxy curcumin, and 2.2-6.5% bis demethoxy curcumin. In another related aspect, the 20% garcinol is obtained from *Garcinia* sp. In a preferred embodiment, the *Garcinia* sp. is *Garcinia indica*. In another related aspect, the mammal is human.

In yet another aspect, the composition is formulated with pharmaceutically/nutraceutically accepted excipients and adjuvants and administered orally in the form of tablets, capsules, syrups, gummies, powders, suspensions, emulsions, chewable, candies or eatables. In another related aspect, the composition comprising 95% Curcuminoids and 20% Garcinol can be formulated with other known ingredients for liver protection.

In another preferred embodiment, the invention discloses a method of therapeutic management of NAFL in mammals, said method comprising steps of administering an effective amount of a composition comprising 95% curcuminoids and 20% Garcinol to said mammals, to bring about the lipolysis of excess fat accumulated in the liver. In a related embodiment, the 95% Curcuminoids and 20% Garcinol in the composition are administered in concentrations of about 10-50 mg/kg bodyweight and 1-10 mg/kg bodyweight respectively.

In another related embodiment, the 95% Curcuminoids are present in the ratio of about 75-81% curcumin, 15-19% demethoxy curcumin, and 2.2-6.5% bis demethoxy Curcumin. In another preferred embodiment, the invention discloses a composition comprising 95% Curcuminoids and 20% Garcinol for the therapeutic management of symptoms associated with NAFL in mammals. In related embodiment, the symptoms of NAFL include abnormal build-up of fat in the hepatocytes.

In a related embodiment, the 95% curcuminoids and 20% Garcinol in the composition are administered in concentrations of about 10-50 mg/kg bodyweight and 1-10 mg/kg bodyweight respectively.

In another related embodiment, the 95% curcuminoids are present in the ratio of about 75-81% curcumin, 15-19% demethoxy curcumin, and 2.2-6.5% bis demethoxy curcumin. In yet another related embodiment, the mammal is human.

In another preferred embodiment, the invention discloses a method of therapeutic management of NASH in mammals, said method comprising steps of administering an effective amount of a composition containing 95% Curcuminoids and 20% Garcinol to said mammals, to bring about the reduction in the symptoms associated with NASH. In related embodiment, the symptoms of NASH include, but not limited to, inflammatory infiltration, elevated liver enzymes and hepatocellular ballooning.

In another related embodiment, the inflammatory markers are selected from the group consisting of, but not limited to, interleukins, TNF-α and TGF-β. In another related embodiment, the liver enzymes are selected from the group consisting of transaminases, aminotransferases and phosphatases. In a related embodiment, the liver enzyme is preferably ALT.

In a related embodiment, the 95% Curcuminoids and 20% Garcinol in the composition are administered in concentrations of about 10-50 mg/kg bodyweight and 1-10 mg/kg bodyweight respectively. In another related embodiment, the 95% curcuminoids are present in the ratio of about 75-81% curcumin, 15-19% demethoxy curcumin, and 2.2-6.5% bis demethoxy curcumin. In yet another related embodiment, the mammal is human. In another preferred embodiment, the invention discloses a composition comprising 95% Curcuminoids and 20% Garcinol for the therapeutic management of symptoms associated with NASH in mammals.

In related embodiment, the symptoms of NASH include, but not limited to, inflammatory infiltration, elevated liver enzymes and hepatocellular ballooning. In another related embodiment, the inflammatory markers are selected from the group consisting of, but not limited to, interleukins, TNF-α and TGF-β. In another related embodiment, the liver enzymes are selected from the group consisting of transaminases, aminotransferases and phosphatases. In a related embodiment, the liver enzyme is preferably ALT.

In a related embodiment, the 95% Curcuminoids and 20% Garcinol in the composition are administered in concentrations of about 10-50 mg/kg bodyweight and 1-10 mg/kg bodyweight respectively. In another related embodiment, the 95% Curcuminoids are present in the ratio of about 75-81% curcumin, 15-19% demethoxy curcumin, and 2.2-6.5% bis demethoxy curcumin. In yet another related embodiment, the mammal is human.

In another preferred embodiment, the invention disclose a method of therapeutic management of liver fibrosis in mammals, said method comprising steps of administering an effective amount of a composition comprising 95% Curcuminoids and 20% Garcinol to said mammals, to bring about the reduction in the markers of liver fibrosis. In related embodiment, the markers of liver fibrosis include, but not limited to, inflammatory cytokines, elevated liver enzymes and hydroxyproline, and pathological deposition of collagen in liver.

In another related embodiment, the inflammatory markers are selected from the group consisting of, but not limited to, interleukins, TNF-α and TGF-β. In another related embodiment, the liver enzymes are selected from the group consisting of transaminases, aminotransferases and phosphatases. In another related embodiment, the liver enzyme is preferably ALT. In a related embodiment, the 95% Curcuminoids and 20% Garcinol in the composition are administered in concentrations of about 10-50 mg/kg bodyweight and 1-10 mg/kg bodyweight respectively. In another related embodiment, the 95% Curcuminoids are present in the ratio of about 75-81% curcumin, 15-19% demethoxy curcumin, and 2.2-6.5% bis demethoxy curcumin. In yet another related embodiment, the mammal is human.

In another preferred embodiment, the invention discloses a composition comprising 95% Curcuminoids and 20% Garcinol for the reduction of symptoms and markers associated with liver fibrosis in mammals. In related embodiment, the markers of liver fibrosis include, but not limited to, inflammatory cytokines, elevated liver enzymes and hydroxyproline, and pathological deposition of collagen in liver. In another related embodiment, the inflammatory markers are selected from the group consisting of, but not limited to, interleukins, TNF-α and TGF-β. In another related embodiment, the liver enzymes are selected from the group consisting of transaminases, aminotransferases and phosphatases.

In a related embodiment, the 95% Curcuminoids and 20% Garcinol in the composition are administered in concentrations of about 10-50 mg/kg bodyweight and 1-10 mg/kg bodyweight respectively. In another related embodiment, the 95% Curcuminoids are present in the ratio of about 75-81% curcumin, 15-19% de methoxy curcumin, and 2.2-6.5% bis de methoxy curcumin. In yet another related embodiment, the mammal is human.

In another most preferred embodiment, the invention discloses a method of providing hepatoprotection in mammals, said method comprising steps of administering effective amounts of a composition comprising 95% Curcuminoids and 20% Garcinol to mammals, to bring about reduction in inflammatory markers and liver enzymes to confer hepatoprotection.

In a related embodiment, the 95% curcuminoids and 20% Garcinol in the composition are administered in concentrations of about 10-50 mg/kg bodyweight and 1-10 mg/kg bodyweight respectively. In another related embodiment, the 95% curcuminoids are present in the ratio of about 75-81% curcumin, 15-19% demethoxy curcumin, and 2.2-6.5% bis demethoxy curcumin. In a related embodiment, the inflammatory markers are selected from the group comprising, but not limited to, interleukins, TNF-α and TGF-β. In another related embodiment, the liver enzymes are selected from the group consisting of transaminases, aminotransferases and phosphatases. In yet another embodiment, the mammal is human.

In another preferred embodiment, the invention discloses a composition comprising 95% Curcuminoids and 20% Garcinol for use as a hepatoprotective agent. In a related embodiment, the 95% Curcuminoids and 20% Garcinol in the composition are administered in concentrations of about 10-50 mg/kg bodyweight and 1-10 mg/kg bodyweight respectively. In another related embodiment, the 95% curcuminoids are present in the ratio of about 75-81% curcumin, 15-19% demethoxy curcumin, and 2.2-6.5% bis demethoxy curcumin. In yet another related embodiment, the mammal is human.

The following illustrative examples are included to understand the technical features and advantages of the present invention.

EXAMPLES

Example 1: Methods

Mice Model

The experiments are carried out on STAM model of NASH-HCC. The NASH STAM model is widely used primarily because it recapitulates the full spectrum of human NAFLD ranging from steatosis to NASH and hepatic fibrosis. In addition, the histological phenotypes observed in this model are like those seen in human clinical samples, which allows the same scoring system (NAFLD activity score; NAS) to be used to assess the severity of the disease (Kazuki Takakura Et al., Mouse models for investigating the underlying mechanisms of non alcoholic steatoheapatitis-derived hepatocellular carcinoma; World J Gastroenterol; 2018 May 14; 24 (18); 1989-1994).

In the STAM mice model there is no weight gain and the animals do not show obesity despite high fat diet feeding.

Protocol

Pathogen-free 14-day-pregnant C57BL/6 mice were obtained from Japan SLC, Inc. (Japan), NASH was established in male mice by a single subcutaneous injection of 200 μg streptozotocin (Sigma, USA) after birth and feeding with a high fat diet (CLEA Japan, Japan) ad libitum after 4 weeks of age (age 28±2 days). Mice were randomized into 4 groups of 8 mice each at 5 weeks of age (age 35±2 days) the day before the start of treatment.

Groups

Group 1 (Vehicle): Eight NASH mice were orally administered vehicle 0.5% methyl cellulose] in a volume of 5 mL/kg once daily from 5 to 9 weeks of age, Group 2 (20% Garcinol): Eight NASH mice were orally administered vehicle supplemented with 20% 20% Garcinol at a dose of 10 mg/kg once daily from 5 to 9 weeks of age, Group 3 (95% Curcuminoids—commercially available Curcumin C3 Complex® from Sabinsa Corporation, USA): Eight NASH mice were orally administered vehicle supplemented with Curcumin C3 complex at a dose of 50 mg/kg once daily from 5 to 9 weeks of age, Group 4 (20% Garcinol and Curcumin C3 Complex®): Eight NASH mice were orally administered vehicle supplemented with 20% 20% Garcinol at a dose of 10 mg/kg and Curcumin C3 complex at a dose of 50 mg/kg once daily from 6 to 9 weeks of age.

Table 1 below summarizes the treatment schedule

TABLE 1

Treatment schedule

| Group | No. Mice | Mice | Test Substance | Dose (mg/kg) | Volume (ml/kg) | Regimen | Sacrifice (wks) |
|---|---|---|---|---|---|---|---|
| 1 | 8 | STAM | Vehicle | — | 5 | PO, QD 5-9 Weeks | 9 |
| 2 | 8 | STAM | 20% Garcinol | 10 | 5 | PO, QD 5-9 Weeks | 9 |
| 3 | 8 | STAM | 95% Curcuminoids | 50 | 5 | PO, QD 5-9 Weeks | 9 |
| 4 | 8 | STAM | 20% Garcinol 95% Curcuminoids | 10 50 | 5 | PO, QD 6-9 Weeks | 9 |

All the animals were humanely sacrificed at 9 weeks of age and the organ weight, Individual liver weight, Liver-to-body weight ratio were recorded.

Sample Collection

For plasma samples, non-fasting blood was collected in polypropylene tubes with anticoagulant (Novo-Heparin) and centrifuged at 1,000×g for 15 minutes at 4° C. The supernatant was collected and stored at −80° C. For frozen liver samples, left medial lobe and caudate lobe were snap frozen in liquid nitrogen and stored at −80° C.

For paraffin-embedded liver blocks, left lateral lobe was collected and cut into 6 pieces. Two pieces of left lateral lobe were fixed in Bouin's solution and then embedded in paraffin.

For cDNA samples, the other 2 pieces of left lateral lobe were snap frozen in liquid nitrogen and stored at −80° C. until use. Total RNA was extracted from liver samples using RNAiso (Takara Bio, Japan) according to the manufacturer's instructions. One μg of RNA was reverse-transcribed using a reaction mixture containing 4.4 mM MgCl2 (F. Hoffmann-La Roche, Switzerland), 40 U RNase inhibitor (Toyobo, Japan), 0.5 mM dNTP (Promega, USA), 6.28 μM random hexamer (Promega), 5× first strand buffer (Promega), 10 mM dithiothreitol (Invitrogen, USA) and 200 U MMLV-RT (Invitrogen) in a final volume of 20 μL. The reaction was carried out for 1 hour at 37° C., followed by 5 minutes at 99° C.

Measurement of Whole Blood and Plasma Biochemistry

Non-fasting blood glucose was measured in whole blood using Stat Strip glucose meter (NIPRO CORPORATION, Japan). For plasma biochemistry, non-fasting blood was collected in polypropylene tubes with anticoagulant (Novo-Heparin, Mochida Pharmaceutical Co. Ltd., Japan) and centrifuged at 1,000×g for 15 minutes at 4° C. The supernatant was collected and stored at −80° C. until use. Plasma ALT and total cholesterol were measured by FUJI DRI-CHEM 7000 (Fujifilm, Japan). The estimation of adiponectin was done according to user's manual from R&D Systems.

Measurement of Liver Biochemistry

Measurement of Liver Triglyceride Content

Liver total lipid-extracts were obtained by Folch's method (Folch J. et al., J. Biol. Chem. 1957; 226: 497). Liver samples were homogenized in chloroform-methanol (2:1, v/v) and incubated overnight at room temperature. After washing with chloroform-methanol-water (8:4:3, v/v/v), the extracts were evaporated to dryness, and dissolved in iso-propanol. Liver triglyceride content was measured by Triglyceride E-test (Wako Pure Chemical Industries, Ltd., Japan).

Measurement of Liver Hydroxyproline Content

To quantify liver hydroxyproline content, frozen liver samples were processed by an alkaline-acid hydrolysis method as follows. Liver samples were defatted with 100% acetone, dried in the air, dissolved in 2N NaOH at 65° C., and autoclaved at 121° C. for 20 minutes. The lysed samples (400 μL) were acid-hydrolyzed with 400 μL of 6N HCl at 121° C. for 20 minutes, and neutralized with 400 μL of 4N NaOH containing 10 mg/mL activated carbon. AC buffer (2.2M acetic acid/0.48M citric acid, 400 μL) was added to the samples, followed by centrifugation to collect the supernatant. A standard curve of hydroxyproline was constructed with serial dilutions of trans-4-hydroxy-L-proline (Sigma-Aldrich) starting at 16 μg/mL. The prepared samples and standards (each 400 μL) were mixed with 400 μL chloramine T solution (Wako Pure Chemical Industries) and incubated for 25 minutes at room temperature.

The samples were then mixed with Ehrlich's solution (400 μL) and heated at 65° C. for 20 minutes to develop the color. After samples were cooled on ice and centrifuged to remove precipitates, the optical density of each supernatant was measured at 560 nm. The concentrations of hydroxyproline were calculated from the hydroxyproline standard curve. Protein concentrations of liver samples were determined using a BCA protein assay kit (Thermo Fisher Scientific, USA) and used to normalize the calculated hydroxyproline values. Liver hydroxyproline levels were expressed as μg per mg protein.

The levels of TNF-α was estimated by cytokine ELISA as described by the manufacturer (R&D systems)

The anti-oxidants glutathione, Glutathione peroxidase and lipid peroxidation were estimated using standard procedures as described by:

Ellman, G L 1959, 'Tissue sulfhydryl groups', Archives Biochemistry Biophysics, vol. 82, pp. 70-77

Paglia, D E & Valentine, W N 1967, 'Studies on the quantitative and qualitative characterization of erythrocyte glutathione peroxidase', Journal of Laboratory and Clinical Medicine, vol. 70, pp. 158-169.

Buege, J A & Aust. S D 1978, 'Microsomal lipid peroxidation', Methods Enzymol, vol. 52, pp. 302-310.

Histological Analyses

For HE staining, sections were cut from paraffin blocks of liver tissue prefixed in Bouin's solution and stained with Lillie-Mayer's Hematoxylin (Muto Pure Chemicals Co., Ltd., Japan) and eosin solution (Wako Pure Chemical Industries). NAFLD Activity score (NAS) was calculated according to the criteria of Kleiner (Kleiner D E. et al., Hepatology, 2005; 41:1313).

To visualize collagen deposition, Bouin's fixed liver sections were stained using picro-Sirius red solution (Waldeck, Germany). For quantitative analysis of fibrosis area, bright field images of Sirius red-stained sections were captured around the central vein using a digital camera (DFC295; Leica, Germany) at 200-fold magnification, and the positive areas in 5 fields/section were measured using ImageJ software (National Institute of Health, USA) SR_SLMN039-1704-08/16.

Statistical Tests

Statistical analyses were performed using Bonferroni Multiple Comparison Test on GraphPad Prism 6 (GraphPad Software Inc., USA). P values<0.05 were considered statistically significant. A trend or tendency was assumed when a one-tailed t-test returned P values<0.1. Results were expressed as mean±SD.

Results

Figure 2:
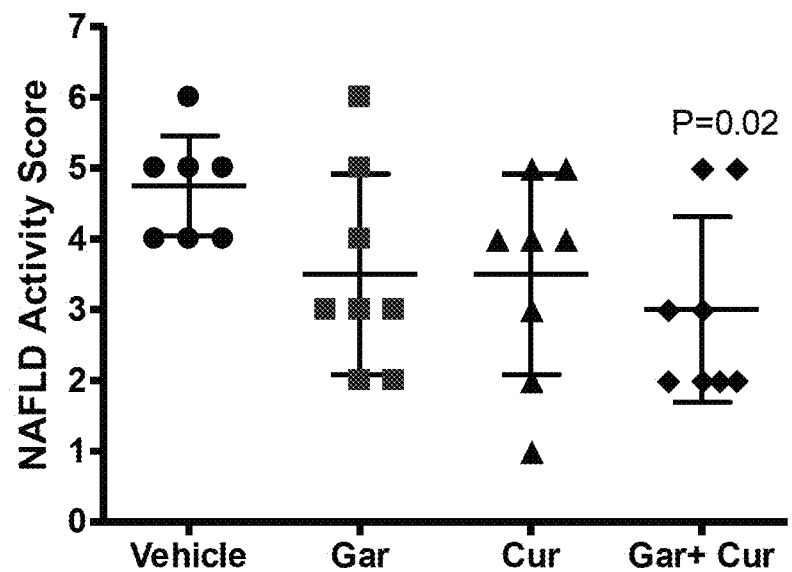
FIG. 2 is a graphical representation showing NAFLD score in liver sections of animals administered with garcinol, curcuminoids and Garcinol+Curcuminoids. NAFLD Score is calculated based on the histological sections stained with haematoxylin and Eosin
Figure 3:
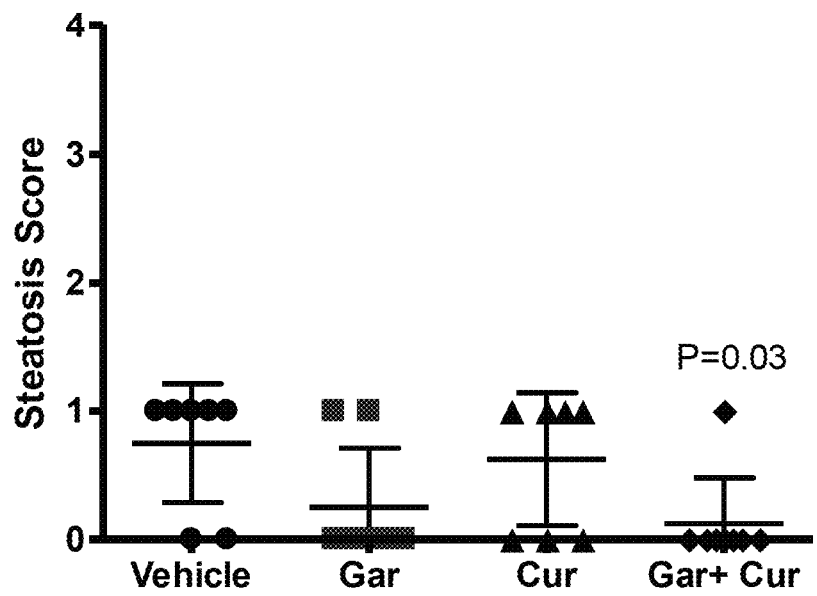
FIG. 3 is a graphical representation showing steatosis score in liver sections of animals administered with garcinol, curcuminoids and Garcinol+Curcuminoids.
Figure 4:
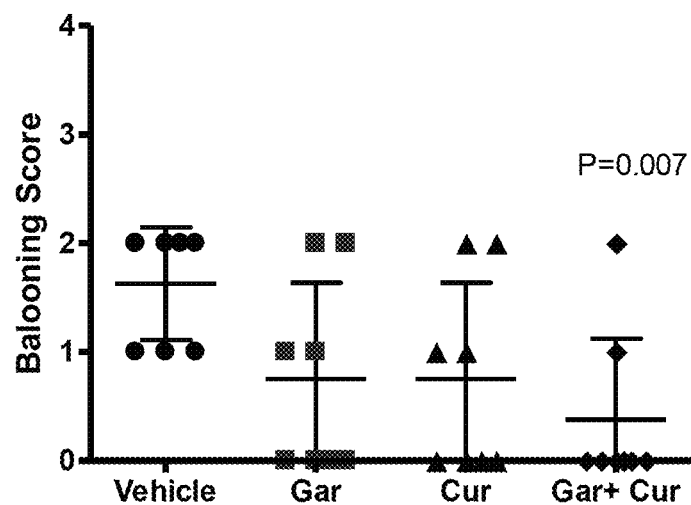
FIG. 4 is a graphical representation showing ballooning score in liver sections of animals administered with garcinol, curcuminoids and Garcinol+Curcuminoids.

Non alcoholic fatty liver (NAFLD) is characterized by hepatic steatosis in the absence of a history of significant alcohol use or other known liver disease. Non alcoholic steatoheapatitis (NASH) is the progressive form of NAFLD. The pathology committee of the NASH Clinical Research designed and validated a histological feature scoring system that addresses the full spectrum of lesions of NAFLD and proposed a NAFLD activity score for use of clinical trials. NAFLD Score is calculated based on the histological sections stained with haematoxylin and Eosin (FIG. 1). Treatment with Garcinol+Curcuminoids showed significant decrease in Fatty liver disease with lower NAFLD score (FIG. 2). Further, Treatment with Garcinol+Curcumin also showed significant decrease in Steatosis (FIG. 3) and Hepatocyte ballooning (FIG. 4).

The results indicated that treatment with a mixture of 20% Garcinol and 95% Curcuminoids showed significant decrease in the NAFLD activity score compared to the untreated control and individual Garcinol 20% and Curcuminoids 20%, thus indicating synergistic decrease in Fatty liver disease and providing synergy between the combination comprising 20% Garcinol and Curcuminoids when administered individually showed lower NAFLD score compared to untreated control but higher than the combination. In steatosis, hepatocyte ballooning is a feature denoting cellular injury and characterised by enlarged, swollen hepatocytes. With respect to the management of NASH, treatment with mixture of 20% Garcinol and Curcuminoids showed significant synergistic decrease in steatosis and Hepatocyte ballooning.

Figure 5:
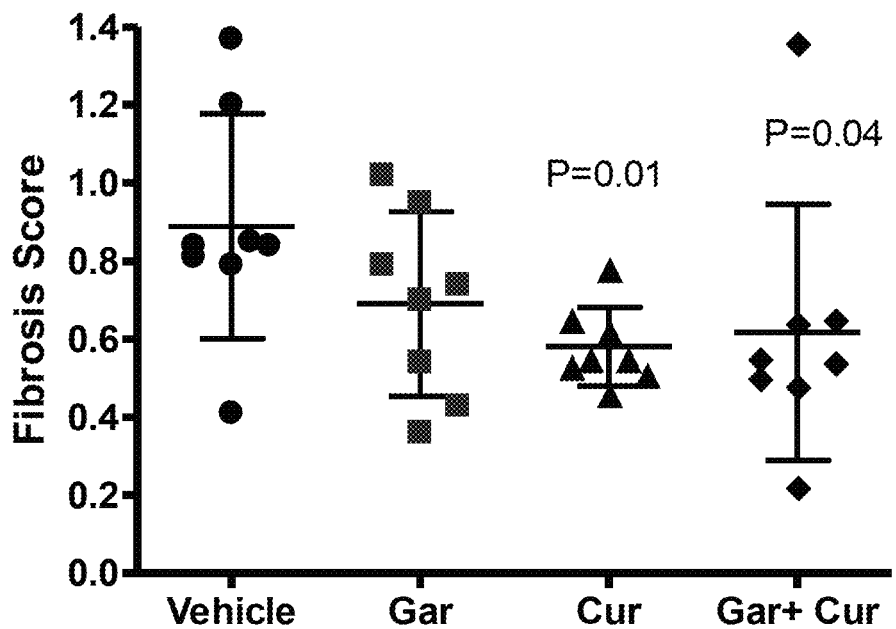
FIG. 5 is a graphical representation showing the area of fibrosis in liver sections of animals administered with garcinol, curcuminoids and Garcinol+Curcuminoids.

Fibrosis in the liver depends on imbalance between the rate of formation and deposition of collagen which associated with many metabolic and biochemical abnormalities. Liver fibrosis is a reactive, benign, or pathological state of the formation of excess fibrous connective tissue, which is a reparative activity to protect the integrity of the liver during pathological conditions. Their level in liver tissues decides the rate and progression of liver fibrogenesis. Its non invasic fibrotic detecting activity serves as a biomarker in chronic liver diseases with severe fibrosis. The area of fibrosis was measured by Sirius red staining of morphometric quantification of liver sections. It was observed that 20% Garcinol and 95% Curcuminoids synergistically reduced the area of fibrosis indicating lower collagen deposit (FIG. 5).

Figure 6:
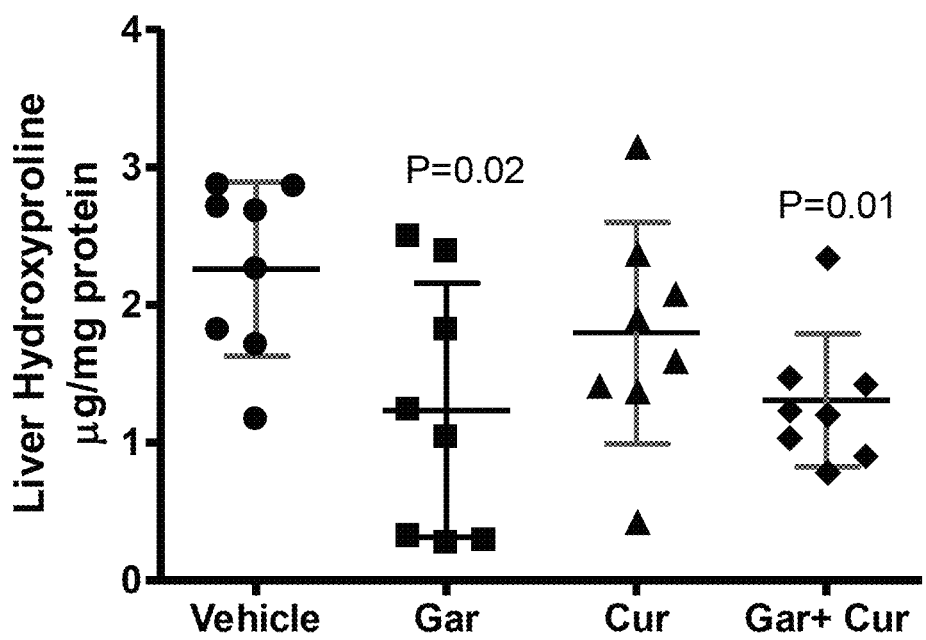
FIG. 6 is a graphical representation showing the liver hydroxyproline levels in animals administered with garcinol, curcuminoids and Garcinol+Curcuminoids.
Figure 7:
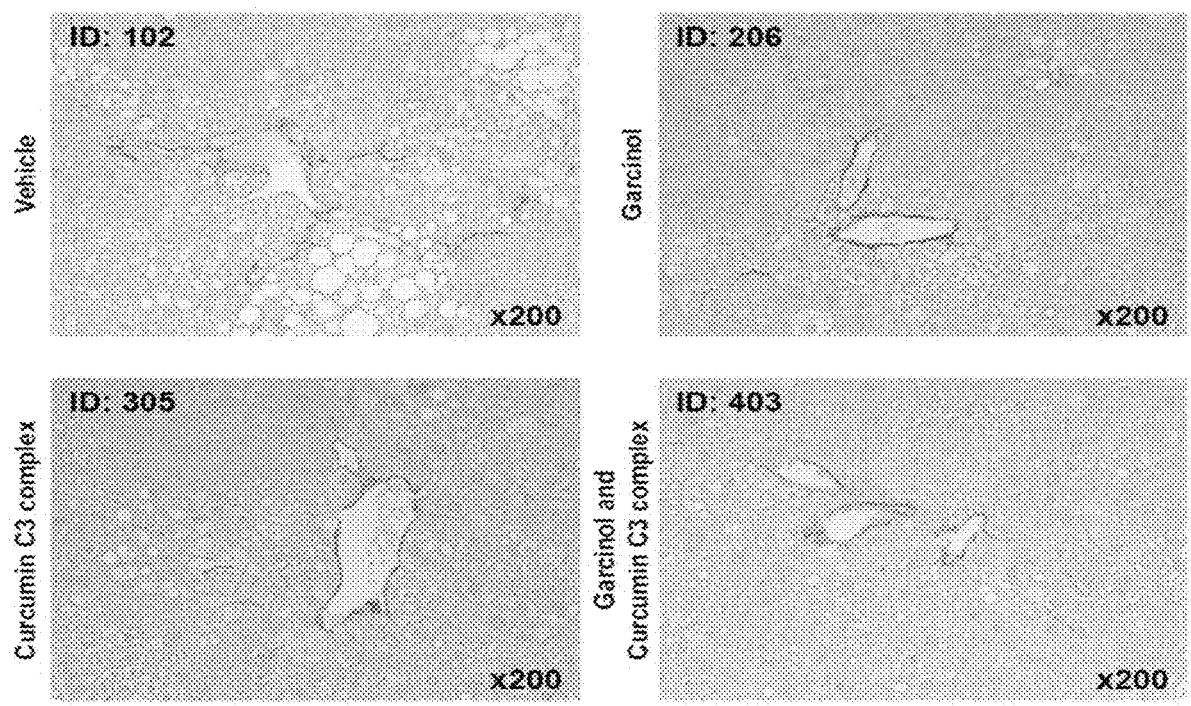
FIG. 7 shows the histopathological micrographs of the liver sections stained with Picrosirius red showing the collagen deposition in animals administered with garcinol, curcuminoids and Garcinol+Curcuminoids.

Hydroxyproline is a major component of fibrillar collagen, comprising ~14% of the total amino acid content. The development of fibrosis depends mainly on incorporation of hydroxyproline into procollagen. Further, hydroxyproline is the only unique amino acid that restricted for the synthesis of collagen fibrils in connective tissues. During collagen degradation, the released hydroxyproline content in liver, urine and serum correlates with fibrosis and can be used as a diagnostic marker for fibrotic scores (Need A G. Bone resorption markers in vitamin D insufficiency; Clin Chim Acta. 2006; 368:48-52.) The treatment of Garcinol-Curcuminoids composition synergistically reduced the hydroxyproline levels (FIG. 6) thus reducing collagen deposition as represented FIG. 7 when stained by Picrosirius red. No change in the body weight and liver weight (Table 2) was observed in all the treatment groups compared to control.

TABLE 2

Body and Liver weight

| Parameter | Vehicle | Garcinol | Curcuminoids | Garcinol and Curcuminoids |
|---|---|---|---|---|
| Body weight (g) | 20.2 ± 1.3 | 20.3 ± 1.5 | 20.9 ± 1.7 | 20.0 ± 2.8 |
| Liver weight (mg) | 1480 ± 140 | 1467 ± 120 | 1584 ± 117 | 1415 ± 183 |
| Liver-to-body weight ratio (%) | 7.4 ± 0.7 | 7.3 ± 0.8 | 7.6 ± 0.9 | 7.1 ± 0.4 |

With regard to the biochemical parameters, there was no change in the levels of plasma glucose, total cholesterol and triglycerides (Table 3) in the treatment groups compared to control. However, plasma ALT levels, which were elevated due to NAFLD, were significantly reduced by the composition containing garcinol and curcuminoids (Table 3) indicating the Hepatoprotective effect of the composition.

TABLE 3

Serum Biochemical parameters

| Parameter | Vehicle | Garcinol | Curcuminoids | Garcinol and Curcuminoids |
|---|---|---|---|---|
| Whole blood glucose (mg/dL) | 533 ± 75 | 564 ± 51 | 560 ± 43 | 605 ± 73 |
| Plasma ALT (U/L) | 51 ± 12 | 56 ± 12 | 56 ± 16 | 47 ± 14 |
| Plasma total cholesterol (mg/dL) | 152 ± 25 | 151 ± 18 | 162 ± 32 | 172 ± 50 |
| Liver triglyceride (mg/g liver) | 57.5 ± 28.9 | 71.8 ± 33.3 | 93.0 ± 27.3 | 76.9 ± 29.8 |

Figure 8:
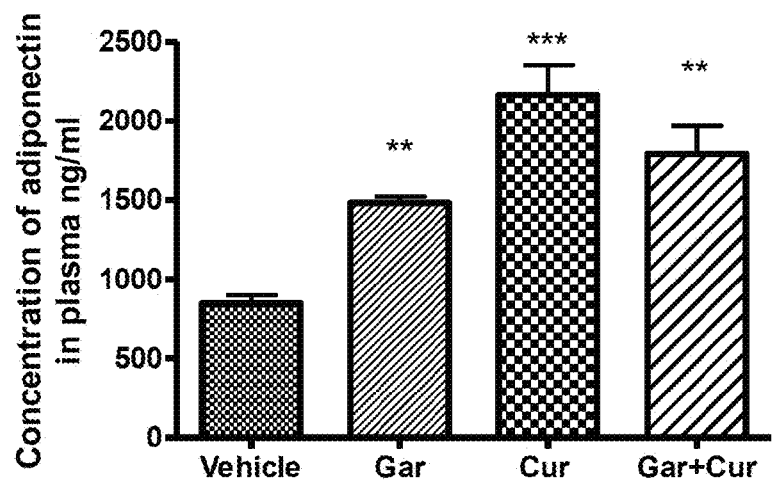
FIG. 8 is the graphical representations showing adiponectin levels in animals administered with garcinol, curcuminoids and Garcinol+Curcuminoids.

Adiponectin controls the metabolism of both glucose and lipids by decreasing gluconeogenesis and increasing glycolysis and fatty acid oxidation. The levels of adiponectin were significantly reduced in NAFLD mice model. The composition comprising garcinol and curcuminoids effectively increase the levels of adiponectin (FIG. 8) conferring hepatoprotection.

Figure 9:
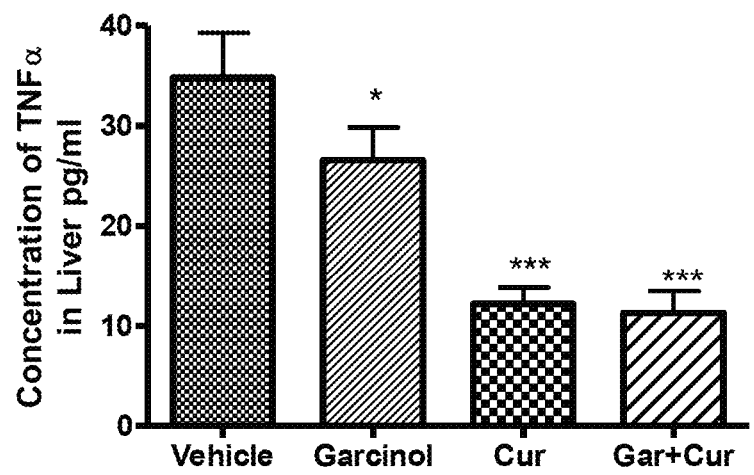
FIG. 9 is the graphical representations showing plasma TNFα levels in animals administered with garcinol, curcuminoids and Garcinol+Curcuminoids.
Figure 10:
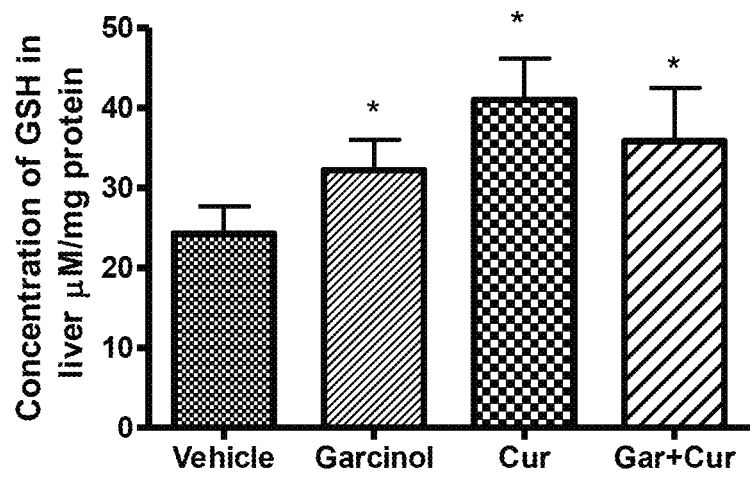
FIG. 10 is the graphical representations showing plasma glutathione levels in animals administered with garcinol, curcuminoids and Garcinol+Curcuminoids.
Figure 11:
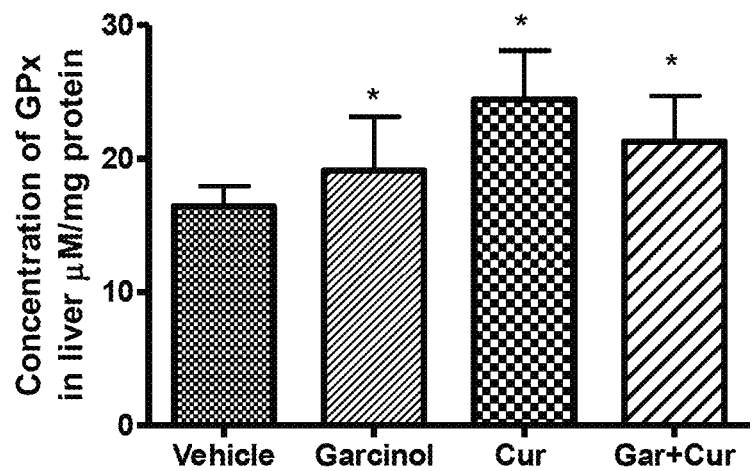
FIG. 11 is the graphical representations showing plasma glutathione peroxidase levels in animals administered with garcinol, curcuminoids and Garcinol+Curcuminoids.
Figure 12:
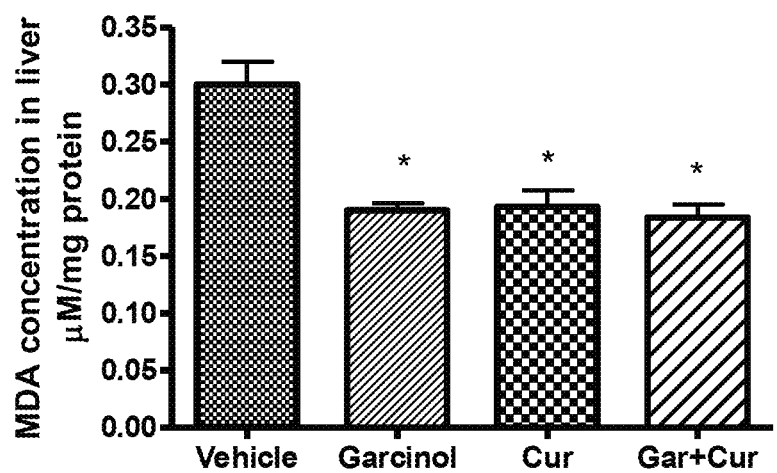
FIG. 12 is the graphical representations showing extent of lipid peroxidation in animals administered with garcinol, curcuminoids and Garcinol+Curcuminoids.

The plasma levels of inflammatory marker, TNF-α were elevated in NAFLD. Curcuminoids and garcinol+curcuminoids composition significantly reduces the levels of TNF-α (FIG. 9). The composition also increased the levels of antioxidants glutathione (FIG. 10) and glutathione peroxidase (FIG. 11) and significantly reduced lipid peroxidation (FIG. 12) indicating its role as an anti-oxidant and anti-inflammatory agent.

Example 2: Gene Expression Studies

The expression of inflammatory markers TNF-α, NFκB, TGF-β and MCP-1, were evaluated.

β-Actin
F-GAAGTCCCTCACCCTCCCAA

R-GGCATGGACGCGACCA

NFκB
F-GAAATTCCTGATCCAGACAAAAAC

R-ATCACTTCAATGGCCTCTGTGTAG

TNF-α
F-CTCCAGGCGGTGCCTATGT

R-GAAGAGCGTGGTGGCCC

MCP-1
F-GCATCCACGTGTTGGCTCA-

R-CTCCAGCCTACTCATTGGGATCA

TGF-β
F-TTGCCCTCTACAACCAACACAA

R-GGCTTGCGACCCACGTAGTA

Collagen1
F-TTCCCTGGACCTAAGGGTACT

R-TTGAGCTCCAGCTTCGCC

Figure 13:
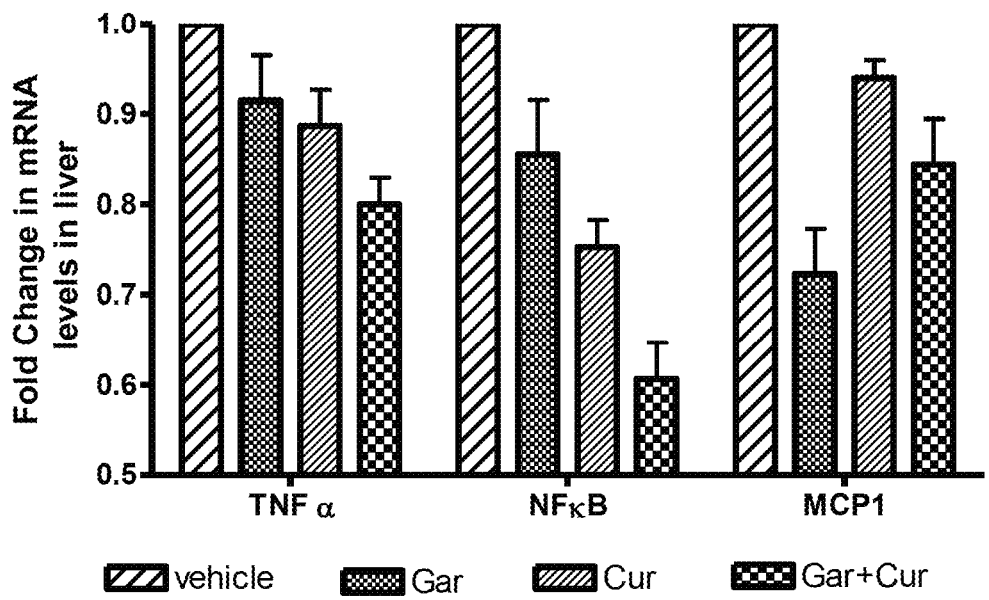
FIG. 13 is the graphical representations showing the expression of TNF-α, NFκB and MCP1 in animals administered with garcinol, curcuminoids and Garcinol+Curcuminoids.
Figure 14:
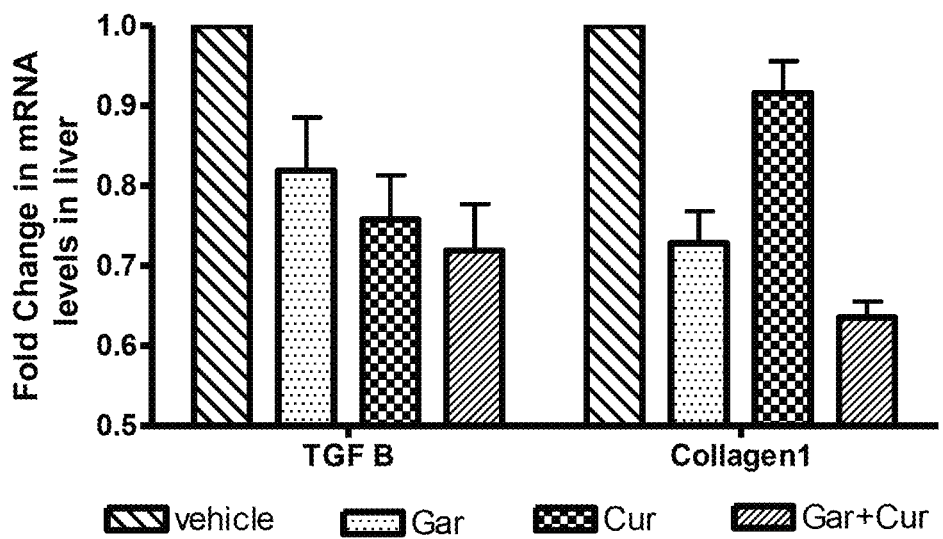
FIG. 14 is the graphical representations showing the expression of TGF-β and collagen1 in animals administered with garcinol, curcuminoids and Garcinol+Curcuminoids.

Expressions of inflammatory markers mainly TNF-α, NFκ B and MCP1 (FIG. 13) are reduced in the liver of treated animals with invention composition. 95% Curcuminoids along with 20% Garcinol showed higher inhibition of TNF-α, NFκ B and MCP1. The expression of TGF-β and collagen1 which are key markers for fibrosis was also significantly reduced by the composition (FIG. 14).

Overall, the composition containing 95% Curcuminoids and 20% Garcinol act synergistically effecting significant reduction in NAFLD, significant decrease in liver hydroxyproline, significant decrease in steatosis, decreasing trend in fibrosis and NASH, reducing hepatocytes ballooning, reduced pathological deposition of collagen in liver thus conferring liver protection.

The present invention discloses the synergistic effects of a composition comprising Curcuminoids and Garcinol for liver protection. A person with ordinary skill in the art would find it obvious when the abovementioned composition is mixed or formulated other ingredients, known or evaluated for liver protection.

Other modifications and variations to the invention will be apparent to those skilled in the art from the foregoing disclosure and teachings. Thus, while only certain embodiments of the invention have been specifically described herein, it will be apparent that numerous modifications may be made thereto without departing from the spirit and scope of the invention. The scope of the invention is to be interpreted only in conjunction with the appended claims.

We claim:

1. A method for the therapeutic management of non-alcoholic fatty liver disease and associated conditions non-alcoholic fatty liver, non-alcoholic steatohepatitis and fibrosis in mammals, said method comprising steps of administering effective amounts of a composition comprising a combination of 95% Curcuminoids containing 75%-81% curcumin, 15-19% demethoxycurcumin and 2.2-6.5% bisdemethoxycurcumin and 20% Garcinol to mammals in need of such therapy, to bring about effect of reducing symptoms of non-alcoholic fatty liver disease and associated conditions non-alcoholic fatty liver, non-alcoholic steatohepatitis and fibrosis.

2. The method as in claim 1, wherein the therapeutic effect is reducing fat deposition in hepatocytes occurring in NAFL.

3. The method as in claim 1, wherein the therapeutic effect is reducing inflammatory infiltration in hepatocytes and hepatocellular ballooning occurring in NASH.

4. The method as in claim 1, wherein the therapeutic effect is reducing elevated hydroxyproline levels and pathological deposition of collagen in liver occurring in fibrosis.

5. The method as in claim 3, wherein the markers for inflammatory infiltration in hepatocytes are selected from the group comprising TNF-α, NFκB, TGF-β and MCP-1.

6. The method as in claim 1, wherein the composition is administered in concentrations of about 10-50 mg/kg bodyweight and 1-10 mg/kg bodyweight respectively.

7. The method as in claim 1, wherein the mammal is human.

8. The method as in claim 1, wherein the composition is formulated with pharmaceutically/nutraceutically accepted excipients and adjuvants and administered orally in the form of tablets, capsules, syrups, gummies, powders, suspensions, emulsions, chewable, candies or eatables.

9. The method as in claim 1 wherein the therapeutic effect is the reduction in blood ALT levels.

10. The method as in claim 1 wherein the therapeutic effect is the increase in blood adiponectin expression.

11. The method as in claim 1 wherein the therapeutic effect is the preventing the progression of non-alcoholic fatty liver to non-alcoholic steatohepatitis.

* * * * *